United States Patent

Orlek et al.

[11] Patent Number: 5,541,194
[45] Date of Patent: Jul. 30, 1996

[54] CERTAIN 1-AZABICYCLO[2.2.1]HEPTANES AND 1-AZABICYCLO[2.2.2]OCTANES

[75] Inventors: Barry S. Orlek; Paul A. Wyman; Harry J. Wadsworth, all of Harlow, England

[73] Assignee: Beecham Group p.l.c., Easom, England

[21] Appl. No.: 369,290

[22] Filed: Jan. 6, 1995

Related U.S. Application Data

[63] Continuation of Ser. No. 72,357, Jun. 3, 1993, abandoned, which is a continuation of Ser. No. 880,489, May 6, 1992, abandoned, which is a continuation of Ser. No. 500,229, Mar. 27, 1990, abandoned, which is a continuation of Ser. No. 287,466, Dec. 20, 1988, abandoned.

[30] Foreign Application Priority Data

Dec. 22, 1987 [GB] United Kingdom .................. 8729806
May 27, 1988 [GB] United Kingdom .................. 8812603
Oct. 13, 1988 [GB] United Kingdom .................. 8824074

[51] Int. Cl.⁶ .................. C07D 453/02; C07D 221/02; A61K 31/44; A61K 31/435
[52] U.S. Cl. .................. 514/299; 514/305; 514/374; 514/378; 514/413; 514/210; 546/133; 546/112; 548/235; 548/247; 548/453; 548/950
[58] Field of Search .................. 546/133, 112; 548/235, 247, 453, 950; 514/210, 299, 305, 374, 378, 413

[56] References Cited

FOREIGN PATENT DOCUMENTS

| | | |
|---|---|---|
| 307141 | 3/1989 | European Pat. Off. . |
| 0307141 | 3/1989 | European Pat. Off. ............... 548/235 |
| 316718 | 5/1989 | European Pat. Off. . |
| 0316718 | 5/1989 | European Pat. Off. ............... 546/112 |

*Primary Examiner*—Alan L. Rotman
*Attorney, Agent, or Firm*—Hopgood, Calimafde, Kalil & Judlowe

[57] ABSTRACT

Novel compounds of formula (I), processes for their preparation, and their use as pharmaceutical agents are described:

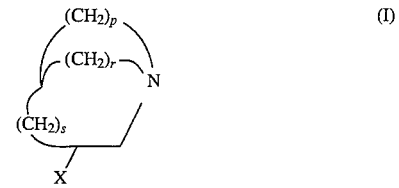

in which p represents an integer of 2 to 4; r represents an integer of 1 or 2; s represents 0 or 1; and X represents a group

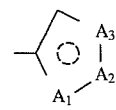

in which $A_1$ is oxygen or sulphur, one of $A_2$ and $A_3$ is $CR_1$ and the other is nitrogen or $CR_2$, or $A_2$ is oxygen or sulphur, $A_1$ is CH and $A_3$ is $CR_1$, where $R_1$ and $R_2$ are independently selected from hydrogen and $C_{1-2}$ alkyl, with the proviso that when r is 2, $R_1$ and $R_2$ are hydrogen or methyl. The novel compounds of this invention may be used to treat or to prevent dementia in mammals.

7 Claims, No Drawings

CERTAIN 1-AZABICYCLO[2.2.1]HEPTANES AND 1-AZABICYCLO[2.2.2]OCTANES

This application is a continuation of application Ser. No. 08/072,357, filed Jun. 3rd, 1993, now abandoned, which is a continuation of application Ser. No. 880,489, filed May 6th, 1992, now abandoned, which is a continuation of application Ser. No. 500,229, filed Mar. 27th, 1990, now abandoned, which is a continuation of application Ser. No. 287,466, filed Dec. 20th, 1988, now abandoned.

This invention relates to compounds having pharmaceutical activity, to a process for their preparation and their use as pharmaceuticals.

EP-A-0 261 763 (Beecham Group p.l.c) discloses a group of non-aromatic 1-azabicyclic ring systems substituted at the 3-position by a 5-membered aromatic heterocycle including inter alia 1,2,4-oxadiazol-5-yl, 1,3,4-oxadiazol-2-yl, 1,2,4-thiadiazol-5-yl and 1,3-oxazol-2-yl, which are disclosed as useful in the treatment and/or prophylaxis of dementia in mammals.

A novel group of compounds has now been discovered which enhance acetylcholine function via an action at muscarinic receptors within the central nervous system and are therefore of potential use in the treatment and/or prophylaxis of dementia in mammals.

Accordingly, the present invention provides a compound of formula (I) or a pharmaceutically acceptable salt thereof:

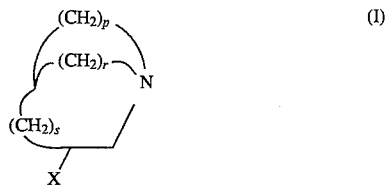

in which p represents an integer of 2 to 4; r represents an integer of 1 or 2; s represents 0 or 1; and X represents a group

in which $A_1$ is oxygen or sulphur, one of $A_2$ and $A_3$ is $CR_1$ and the other is nitrogen or $CR_2$, or $A_2$ is oxygen or sulphur, $A_1$ is CH and $A_3$ is $CR_1$, where $R_1$ and $R_2$ are independently selected from hydrogen and $C_{1-2}$ alkyl, with the proviso that when r is 2, $R_1$ and $R_2$ are independently hydrogen or methyl.

In compounds of formula (I) having two assymetric centres, the stereo-chemical configuration in which the group X and the $(CH_2)_r$ bridge are on the same side of the plane of the molecule which contains both bridgehead atoms and the ring carbon atom bonded to the group X will herein be referred to as the exo configuration. Similarly the configuration of compounds in which the group X and the bridge $(CH_2)_r$ are on opposite sides of the above-mentioned plane of the molecule will herein be referred to as the endo configuration. Preferably compounds of formula (I) have the exo configuration.

The compounds of formula (I) are capable of existing in enantiomeric forms. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Preferred combinations of (p,r,s) include (2,2,0), (2,1,1), (3,1,1), (2,1,0) and (3,1,0).

5-Membered aromatic heterocycles within the definitiion of variable X include oxazole such as 1,2-oxazol-5-yl and 1,3-oxazol-5-yl and furan such as furan-2-yl and furan-3-yl.

Examples of X include 1,2-oxazol-5-yl,3-methyl-1,2-oxazol- 5-yl, 1,3-oxazol-5-yl, 2-methyl-1,3-oxazol-5-yl, 2-ethyl-1,3-oxazol-5-yl, furan-2-yl, 5-methyl-furan- 2-yl and furan-3-yl.

The invention also provides a process for the preparation of a compound of formula (I), or a pharmaceutically acceptable salt thereof, which process comprises:

(a) cyclising a compound of formula (II):

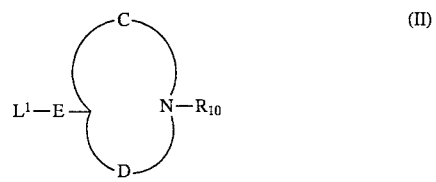

where $R_{10}$ is hydrogen or an N-protecting group, and either C is one, D is another and E is the remainder of $—(CH_2)_p—$, $—(CH_2)_r—$ and $—(CH_2)_s—CHX'—CH_2—$ or groups convertible thereto, X' is X or a group convertible thereto and $L^1$ is a leaving group, or C is one and E is the other of $—(CH_2)_p—$ and $—(CH_2)_r—$ or groups convertible thereto and D represents $—(CH_2)_s—CHX''—CH_2—$ where X'' and $L^1$ together represent $—COO—$, and thereafter, optionally or as necessary and in any appropriate order, converting C, D and E to $—(CH_2)_p—$, $—(CH_2)_r—$ and $—(CH_2)_s—CHX'—CH_2—$, removing any $R_{10}$ protecting group, converting X' to X, interconverting X and/or forming a pharmaceutically acceptable salt, or (b) cyclising a compound of formula (III):

where F is one and G is the other of $—(CH_2)_p—$ and $—(CH_2)_r—$ or groups convertible thereto, and one of $Y^3$ and $Y^4$ is $—(CH_2)_m—W$ and the other is $—(CH_2)_n(CO)_qL^2$ where W is an electron withdrawing group, $L^2$ is a leaving group, m is 1 or 2, n is 0 or 1 and q is 0 or 1, with the proviso that, when $Y^4$ is $—(CH_2)_n(CO)_q L^2$, n and q are each 1, and thereafter, optionally or as necessary and in any appropriate order, hydrolysing and decarboxylating the cyclisation product and converting the carbonyl group to CHX' where X' is X or a group convertible thereto, converting W to X' as defined, converting X' to X, converting F and G to $—(CH_2)_p—$ and $—(CH_2)_r—$ as appropriate, interconverting X and/or forming a pharmaceutically acceptable salt, with the proviso that m, n and q are such that the desired compound of formula (I) is obtained.

Examples of leaving groups $L^1$ include halo such as chloro and hydroxy. Examples of $L^2$ include halo such as chloro or, when q is 1, $C_{1-4}$ alkoxy such as ethoxy. Examples of electron withdrawing groups W include $C_{1-4}$ alkoxycarbonyl and cyano. In the group $-(CH_2)_s-CHX'-CH_2-$, examples of X' include hydroxy and cyano.

In the process variant (a), where $L^1$ is hydroxy and D is $-CHOH-CH_2-$, the cyclisation may be carried out by pyrolysis, by the method of D. O. Spry and H. S. Aaron, J. Org. Chem., 1969, 34, 3674, to yield a compound where X' is hydroxy.

Where E is $-(CH_2)_sCOCH_2-$, the cyclisation may be carried out under basic conditions where $R_{10}$ is benzyl (F. I. Carrol, A. M. Ferguson, and J. B. Lewis, J. Org. Chem. 31, 2957, 1966). The resulting ketone may be reacted with tosylmethyl isocyanide to yield a compound where X' is cyano.

Where $L^1$ and X" together represent $-COO-$, the cyclisation is a rearrangement reaction which can be carried out under acid conditions in a polar solvent, such as hydrogen bromide in ethanol, at ambient temperature, to yield a compound where X' is a carboxy ester group. It is preferred to protect the nitrogen atom with an $R_{10}$ N-protecting group such as benzyl, which may be subsequently removed by hydrogenation over a suitable catalyst such as Pd/C.

In the process variant (b), where $Y^3$ and $Y^4$ both contain carboxy ester groups the cyclisation is a Dieckmann reaction which is catalysed by a base such as potassium t-butoxide at elevated temperature in a solvent such as toluene.

The resulting β-keto ester is hydrolysed and decarboxylated under conventional conditions such as heating at reflux in dilute hydrochloric acid.

The carbonyl group may then be reduced to an X' hydroxy group with a suitable reducing agent such as sodium borohydride in ethanol at ambient temperature, or sodium in ethanol at elevated temperature, such as the boiling point of the solvent, under an inert atmosphere such as nitrogen, depending upon the stereochemistry required.

Alternatively, the carbonyl group may be converted to an X' cyano group with a suitable reagent such as tosylmethylisocyanide in an inert solvent such as dry dimethoxyethane, at depressed temperature, under basic conditions such as the presence of potassium t-butoxide.

Where q is 0, the cyclisation may be carried out as described in EP-0094742 under basic conditions such as sodium hydride and potassium t-butoxide, in an inert polar solvent such as dimethyl formamide.

The conversions of the groups W and X', and interconversions of X, may be carried out conventionally with regard to the group X, see for example standard text books on heterocyclic chemistry such as 'Comprehensive Heterocyclic Chemistry', A. R. Katritzky and C. W. Rees, Pergamon, 1984.

The X' or W group is first converted, as necessary, to a suitable starting group X' for the chosen conversion reaction to give the required group X.

An X' hydroxy group may be converted to cyano by first converting it to a good leaving group such as mesyloxy or tosyloxy and then displacing it with cyanide ion.

An X' cyano group may be converted to $CH_3CO-$ by treatment with methyl lithium in ether at depressed temperature.

An X' cyano or carboxylic acid derivative group such as alkoxycarbonyl or N-methoxy-N-methylamido may be converted to $-CHO$ by controlled reduction using a suitable reducing agent such as diisobutylaluminium hydride in an inert solvent such as toluene at low temperature.

An X' carboxy group may be obtained by conventional de-esterification of an X' or W alkoxycarbonyl group. Where $R_{10}$ is an N-protecting group and X' or W is a benzyloxycarbonyl group, the de-esterification and deprotection steps may conveniently be effected simultaneously by conventional hydrogenation such as described above. Alternatively, an X' carboxy group may be obtained by conventional acid or base hydrolysis of an X' or W cyano group.

An X' chlorocarbonyl group may be obtained by treatment of an X' carboxy group with thionyl chloride at elevated temperature.

An X' $CH_3CO-$ group may be obtained by reaction of a chlorocarbonyl group with N,O-dimethylhydroxylamine and treatment with methyl lithium.

When X represents 1,2-oxazol-5-yl, the reaction of an X' $CH_3CO$ group may be carried out at depressed temperature with ethyl formate in a suitable solvent such as toluene, under basic conditions such as sodium hydride and catalytic ethanol, followed by reflux, to yield the sodium salt of the keto aldehyde (Iva):

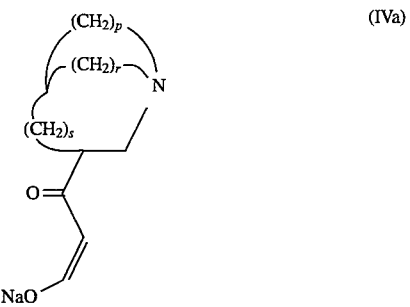

Subsequent cyclisation of the compound of formula (Iva) at ambient temperature with an aminating agent such as hydroxylamine-0-sulphonic acid in a dry solvent such as methanol, ethanol or diglyme, preferably in the presence of an acid such as sulphuric acid, p-toluene sulphonic acid or potassium hydrogen sulphate to minimise amination of the azabicycle, yields a compound of formula (I).

Alternatively, the compound of formula (Iva) may be treated prior to the cyclisation step with dimethylamine in ethanol in the presence of glacial acetic acid at ambient temperature to give the vinylogous amide (IVb):

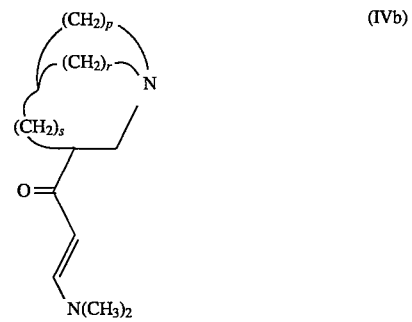

which may be cyclised as described above for the compound of formula (IVa).

3-($C_{1-2}$ alkyl)-substituted 1,2-oxazol-5-yl groups may be prepared analogously using the appropriately substituted analogue of the compound of formula (Iva) prepared by reaction of an X' $CH_3CO$ group with ethyl acetate or ethyl propionate.

When X represents 1,3-oxazol-5-yl, the reaction of an X' $-CHO$ group may be carried out by treatment with tosylmethylisocyanide in a hydroxylic solvent such as methanol, in the presence of a base such as potassium carbonate at elevated temperature. The resulting 4-methoxy-oxazoline can be isolated and purified by distillation. This can in turn be converted to 1,3-oxazol-5-yl by heating in polyphosphoric acid at 160° C. for 10 minutes.

When X represents a 2-substituted 1,3-oxazol-5-yl group, an X'—COCH₃ group may first be converted to a —COCH₂Br group by treatment with bromine in a suitable solvent such as methanol, the nitrogen of the azabicycle being protected as the hydrochloride or hydrobromide salt, or with lithium diisopropylamide and trimethylsilyl chloride at low temperature followed by N-bromosuccinimide in tetrahydrofuran at low temperature. Alternatively, an X' —COCl group may first be converted to a —COCH₂Br group by treatment with diazomethane in ether at low temperature followed by hydrogen bromide in acetic acid at ambient temperature.

The —COCH₂Br group may then be converted to —COCH₂NH₂ by treatment with NaN₃ in acetone followed by hydrogenation over a Pd/C catalyst in ethanolic HCl, or by treatment with hexamethylene tetramine followed by hydrolysis in methanolic HCl.

The —COCH₂NH₂ group may then be acylated with the appropriate derivative of a C₂₋₃ alkanoic acid such as the anhydride or chloride to yield the acyl amino ketone (IVc):

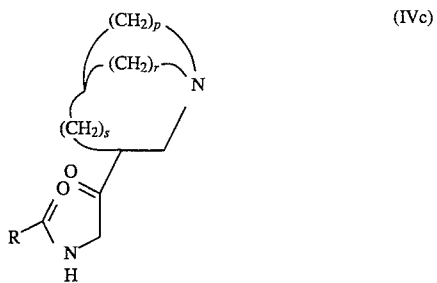

which can be cyclised using a suitable dehydrating agent such as polyphosphoric acid, sulphuric acid or phosphorous pentachloride at elevated temperature.

When X represents 2-furyl, an X' CHO group may be treated with a reactive derivative of propanal such as the 3-tosyl derivative and in which the carbonyl group is preferably protected as a cyclic acetal (V):

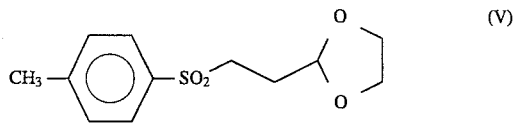

prepared by reaction of sodium 4-methylphenylsulphinate with 2-(2-bromoethyl)-1,3-dioxolane in dimethyl formamide at ambient temperature. The reaction of the compound of formula (V) with the X' CHO group in an inert solvent such as tetrahydrofuran in the presence of a base such as n-butyl lithium, initially at low temperature, rising to ambient, yields a compound of formula (IVd):

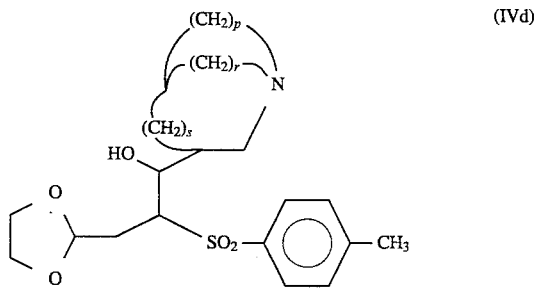

which may be cyclised at elevated temperature in the presence of an acid such as glacial acetic acid, which may also function as the solvent.

Alkyl-substituted furyl groups may be obtained analogously using the appropriately substituted analogue of the compound of formula (V) prepared from the corresponding ketone or aldehyde.

When X represents a 2- or 3-furyl group, an azabicyclic ketone may be treated with a furan derivative lithiated at the 2- or 3-position, prepared by reaction of a furan or 3-bromofuran derivative with n-butyllithium in an inert solvent such as diethylether at reduced temperature, followed by reduction of the resulting alcohol intermediate using triethylsilane in acetonitrile in the presence of a Lewis acid such as stannic chloride or boron trifluoride etherate.

An X 1,3-thiazol-5-yl group may be obtained by dehydrating and cyclising a compound of formula (IVc) using phosphorous pentasulphide at elevated temperature.

Optionally 3-substituted 1,2-thiazol-5-yl groups may be prepared from the corresponding oxazolyl group by ring opening effected by treatment with a reducing agent such as Raney nickel and hydrogen in a suitable solvent such as methanol or ethanol to yield a vinylogous amide of formula (IVe):

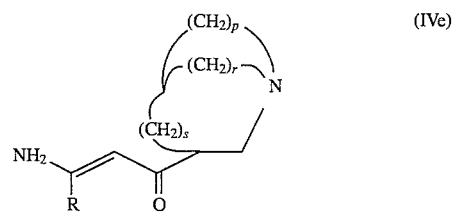

which may be cyclised using phosphorous pentasulphide in the presence of a suitable oxidising agent such as sulphur or chloranil in a solvent such as toluene at elevated temperature.

In formulae (IVa) to (IVe), the variables are as defined in formula (I). In the above description, R represents methyl or ethyl as appropriate.

Where required, the endo isomer may be obtained or isolated at any convenient stage after the cyclisation of the compound of formula (II) or (III). However, the preparation of the endo isomer is preferably effected before the introduction of the required group X. Thus, for example, where the compound of formula (I) has the values (p,r,s) of (2,1,0), and the process variant (a) where L¹ and X" together represent —COO— is employed, the resulting carboxy ester intermediate having the exo configuration may be subjected to an epimerisation reaction by treatment with the appropriate alkali metal alkoxide, for example sodium ethoxide. The resulting mixture of endo and exo isomers may then be separated by chromatography and the endo isomer used for further transformations of the alkoxycarbonyl group X'. In some cases the cyclisation of the compound of formula (III) followed by the conversion of the resulting carbonyl group to CHX' yields a mixture of exo and endo isomers which are conveniently separated by chromatography at a later stage, after subsequent transformations.

The invention also provides a process for the preparation of a compound of formula (I), or a pharmaceutically acceptable salt thereof, which process comprises reacting a compound of formula (VI):

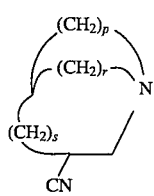

wherein p, r and s are as defined in formula (I), to convert the cyano group into a group X as defined in formula (I), and thereafter, optionally forming a pharmaceutically acceptable salt.

Conversions of the cyano group are as described for conversions of X' cyano groups described above.

Intermediates of formulae (II), (III) and (VI) are known compounds (e.g. as described in EP-A-0094742) or may be prepared analogously.

Intermediates of formula (II) where X" and $L^1$ together represent —COO— are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

Intermediates of formula (II) where $L^1$ is a leaving group are described in, for example, Spry et al., J. Org. Chem., 1969, 34, 3674 and Hasse et al., Chem. Ber., 1960, 93, 1686.

Intermediates of formula (III) are described in, for example, Martell et al., J. Pharm. Sci., 1963, 52(4), 331, Sternbach et al., J.A.C.S., 1952, 74, 2215, Thill et al., J. Org. Chem., 1968, 33, 4376 and EP-0 094 742.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.01 to 10 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

The invention also provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

(±) 3-Cyano-1-azabicyclo[2.2.2]octane (D1)

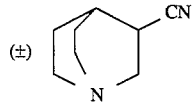

A mixture of 3-quinuclidinone (12.5 g; 0.10 mole), tosylmethyl isocyanide (25.4 g; 0.13 mole) and dry ethanol (10 ml; 0.17 moles) in dry dimethoxyethane (350 ml) was cooled in ice and treated portionwise with potassium t-butoxide (28.0 g; 0.25 moles) while maintaining the temperature between 5° C. and 10° C. After addition was complete the ice bath was removed and stirring was continued for a further 30 min. The reaction was then heated at 40° C. for 2.5 h. After cooling the precipitate was filtered off and the filtrate concentrated in vacuo. Purification on neutral alumina (Brockmann grade 1) using 2% methanol in ethyl acetate as eluant afforded the title compound (D1) as a syrup (10.0 g; 74%) which crystallised on cooling.

DESCRIPTION 2

(±) 3-Acetyl-1-azabicyclo[2.2.2]octane (D2)

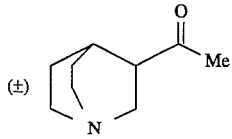

To a solution of (±) 3-cyano-1-azabicyclo[2.2.2]octane (D1, 10.0 g; 0.07 mole) in dry ether (125 ml) cooled to 0° C. under nitrogen was added methyl lithium (67 ml of a 1.5M solution in ether; 0.10 mole) over 15 min. After 2 h at 0° C. the reaction was quenched with 125 ml of 5N sulphuric acid and stirred for a further 3 h at ice temperature. After separation of the ether layer, the aqueous phase was saturated with potassium carbonate and extracted into chloroform (4×100 ml). The combined extracts were dried (Na$_2$SO$_4$) and concentrated in vacuo to give 11.5 g of crude ketone. Purification on neutral alumina using ethyl acetate-cyclohexane (1:1) as eluant afforded the title compound (D2) as a colourless oil which solidified on cooling (7.0 g; 64%).

DESCRIPTION 3

(±) 3-Oxo-3-(1-azabicyclo[2.2.2]oct-3-yl)propanal sodium salt (D3)

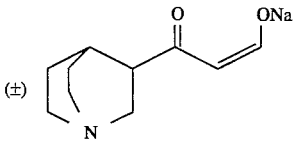

A solution of (±) 3-acetyl-1-azabicyclo[2.2.2]octane (D2) (2.7 g; 0.0175 mole) in dry toluene (75 ml) was treated at ice temperature under nitrogen with sodium hydride (0.58 g of an 80% dispersion in oil; 0.019 mole) and a catalytic amount of ethanol. Ethyl formate (2.8 ml; 0.035 mole) was added dropwise. After stirring at ice temperature for 1 h the reaction was allowed to warm to room temperature and then refluxed for 4 h. The cooled reaction was diluted with dry ether. Filtration afforded the title compound (D3) as a cream coloured solid (3.1 g; 87%) which was used in the next stage without further purification.

DESCRIPTION 4

(±) 1-Azabicyclo[2.2.2]oct-3-ylcarboxaldehyde (D4)

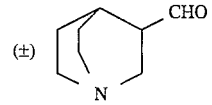

Method (a) Preparation via 3-cyano-1-azabicyclo[2.2.2]octane.

A stirred solution of (±) 3-cyano-1-azabicyclo[2.2.2]octane (D1, 2.1 g, 0.0154 mole) in dry toluene (50 ml) was cooled to −65° C. under nitrogen and treated over 20 minutes with a 1.5M solution of diisobutylaluminium hydride in toluene (13.3 ml, 0.020 mole). The solution was stirred at this temperature for 20 minutes, then allowed to warm up to room temperature over 2 h, before adding 10% sodium hydroxide solution (50 ml) and extracting with chloroform (3×60 ml). The combined organic extracts were dried (Na$_2$SO$_4$) and concentrated in vacuo to give a beige semi-solid (2.3 g), of which approximately 50% was the title compound (D4). The majority of the remaining 50% was starting material (D1). This mixture was used without purification.

Method (b) Preparation via N-methyl-N-methoxycarboxamide.

Diisobutyl aluminium hydride (34 ml of a 1.5 molar solution in toluene, 0.052 mole) was added dropwise to a solution of (±) 1-azabicyclo[2.2.2]oct-3-yl-N-methyl-N-methoxy carboxamide (D22) (5.14 g, 0.026 mole) in dry tetrahydrofuran (170 ml) at −60° C. under nitrogen. The reaction was allowed to warm to −10° C. over a period of 1 h and then quenched by addition to ice cold, well stirred, hydrochloric acid (50 ml, 2M). The solution was then concentrated in vacuo to low volume and basified with solid potassium carbonate. The resulting solid mass was treated with aqueous potassium sodium tartrate and the product recovered by repeated extraction with chloroform. The organic phase was separated, dried over sodium sulphate and concentrated in vacuo to a gum. This was dissolved in ether and filtered to afford a brown oil which was distilled (b.p. 150° C. at 0.5 mmHg) to afford the title compound (D4, 1.92 g, 54%).

$^1$H NMR (CDCl$_3$) δ: 1.35–1.8 (4H, m, 5-CH$_2$, 8-CH$_2$), 2.55 (1H, m, 4-CH), 2.7–3.1 (6H, m, 2-CH$_2$, 7-CH$_2$, 6-CH$_2$), 3.38 (1H, m, 3-CH), 9.8 (1H, s, CHO).

$^{13}$C NMR (CDCl$_3$) δ: 22.5, C-4 and C-5; 27, C-8; 46.5, 47 and 47.5, together C-2, C-6, C-7; 49.5, C-3; 204, C-9.

DESCRIPTION 5

2-[2-(4-Methylphenylsulphonyl)ethyl]-1,3-dioxolane (D5)

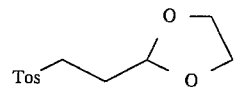

A suspension of sodium 4-methylphenylsulphinate monohydrate (37.2 g, 0.19 mole) in DMF (100 ml) was treated with 2-(2-bromoethyl)-1,3-dioxolane (20 ml, 0.17 mole) and the mixture stirred at room temperature for 64 h. The clear solution was poured into 1000 ml of ice/water containing 100 ml of ammonium hydroxide solution. The mixture was stirred vigorously and the precipitated material solidified. This product was filtered off, washed with water, dried and recrystallised from 2-propanol/ether to give the title compound (D5) as a white crystalline solid (28.7 g, 66%) m.p. 78°–80° C.

¹H Nmr (CDCl₃) δ: 1.75–2.20 (2H, m), 2.42 (3H, s), 2.95–3.35 (2H, m), 3.70–3.95 (4H, m), 4.88 (1H, t, J=4Hz), 7.15–7.40 (2H, m), 7.60–7.85 (2H, m).

DESCRIPTION 6

(±) 2-[3-(1-Azabicyclo[2.2.2]oct-3-yl)-3-hydroxy-2-(4-methylphenylsulphonyl)propyl]-1,3-dioxolane (D6)

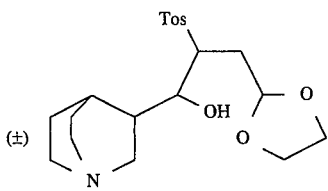

A solution of 2-[2-(4-methylphenylsulphonyl)-ethyl]-1,3-dioxolane (D5, 4.35 g, 0.017 mole) in dry THF (100 ml) at −60° C. under nitrogen was treated with a 1.6M solution of n-butyllithium in hexane (10.0 ml, 0.016 mole) and stirred for 10 minutes. The mixture was then treated with a solution of crude (±)-1-azabicyclo[2.2.2]oct-3-ylcarboxaldehyde (D4, 2.3 g) in dry THF (20 ml) and the mixture allowed to warm up to room temperature over 1.5 h. The solution was treated with saturated potassium carbonate solution and extracted with chloroform (3×80 ml). The combined extracts were dried (Na₂SO₄) and concentrated in vacuo to leave a viscous orange oil (7.7 g), which contained the title compound (D6). This material was used without purification.

DESCRIPTION 7

2-Methyl-2-[2-(4-methylphenylsulphonyl)ethyl]-1,3-dioxolane (D7)

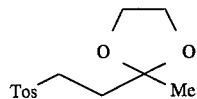

A stirred slurry of 4-methylphenylsulphinic acid (23.7 g, 0.15 mole) in ethylene glycol (30 ml) was treated over 10 min with methyl vinyl ketone (6.3 ml, 0.075 mole) and then stirred at room temperature for 24 h. The mixture was poured into ice/water (1000 ml) containing 5M ammonium hydroxide solution (100 ml) and stirred vigorously for 15 min. The white precipitate was filtered off, washed with water, dried and recrystallised from 2-propanol/60–80 petrol to give the title compound (D7) as a white crystalline solid (15.2 g, 75%) m.p. 122°–123° C.

¹H Nmr (CDCl₃) δ: 1.28 (3H,s), 2.00–2.10 (2H,m), 2.45 (3H,s), 3.13–3.23 (2H,m), 3.80–3.95 (4H,m), 7.32–7.40 (2H,m), 7.75–7.82 (2H,m).

DESCRIPTION 8

(±)2-[3-(1-Azabicyclo[2.2.2]oct-3-yl)-3-hydroxy-2-(4-methylphenylsulphonyl)propyl]-2-methyl-1,3-dioxolane (D8)

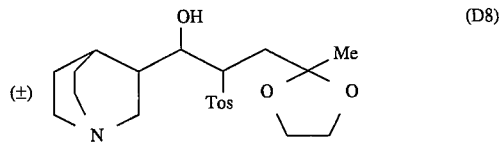

A stirred suspension of 2-methyl-2-[2-(4-methylphenylsulphonyl)ethyl]-1,3-dioxolane (D7, 5.4 g, 0.020 mole) in dry THF (150 ml) at −60° C. under nitrogen was treated with 1.6M n-butyllithium in hexane (11.9 ml, 0.019 mole) and the mixture allowed to warm up to 0° C. to give a homogenous solution. This was then cooled to −60° C. and treated with a solution of crude (±) 1-azabicyclo[2.2.2]oct-3-ylcarboxaldehyde (D4, 2.4 g) in dry THF (20 ml) and the solution allowed to warm up to room temperature over 30 min. The mixture was treated with saturated potassium carbonate solution and extracted with chloroform (3×100 ml). The combined extracts were dried (Na₂SO₄) and concentrated in vacuo to give a crystalline beige solid (11.1 g), which contained the title compound (D8). This material was used without purification.

DESCRIPTION 9

(±) exo-Ethyl 1-azabicyclo[2.2.1]hept-3-ylcarboxylate (D9)

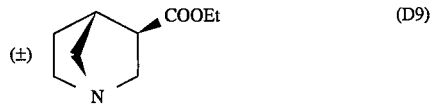

(±)exo-Ethyl 1-benzyl-1-azoniabicyclo[2.2.1]hept-3-ylcarboxylate bromide (EP A 0257741 Description 9) (54 g, 0.16 mole) was dissolved in ethanol (400 ml) and hydrogenated over 10% Pd-C (8.5 g) at atmospheric pressure and 25° C. After 2 h the solution was filtered and concentrated in vacuo to leave a gum. This was partitioned between chloroform and saturated aqueous potassium carbonate solution and the organic phase separated, dried (Na₂SO₄) and concentrated in vacuo to leave a gum. This gum was distilled to give the title compound (D9) as a colourless oil (23 g, 85%) b.p. 150° C. at 0.5 mm.

¹H Nmr (CDCl₃) δ 1.10–1.20 (1H,m), 1.25 (3H,t,J=7Hz), 1.54–1.67 (1H,m), 2.15–2.25 (1H,m), 2.28–2.35 (1H,m), 2.38–2.50 (1H,m), 2.60–2.67 (1H,m), 2.70–2.90 (3H,m), 2.93–3.03 (1H,m), 4.13 (2H,q,J=7Hz).

DESCRIPTION 10

(±) exo-1-Azabicyclo[2.2.1]hept-3-ylcarboxaldehyde (D10)

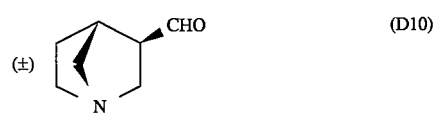

Method (a) Preparation via ethyl carboxylate

A stirred solution of (±) exo-ethyl 1-azabicyclo[2.2.1]hept-3-ylcarboxylate (D9, 1.7 g, 0.010 mole) in dry toluene (50 ml) at −65° C. under nitrogen was treated with 1.5M diisobutylaluminium hydride in toluene (9.2 ml, 0.014 mole) and stirred at −65° C. for 4 h. The solution was treated with glacial acetic acid (3 ml) and allowed to warm up to room temperature, then basified with 10% sodium hydroxide solution, saturated with potassium carbonate and extracted with chloroform (3×60 ml). The combined extracts were dried (Na$_2$SO$_4$) and concentrated in vacuo to give a colourless oil (1.0 g), which contained the title compound (D10). This was used without purification.

Method (b) Preparation via N-methyl-N-methoxycarboxamide

A solution of (±) exo-1-azabicyclo[2.2.1]hept-3-yl-N-methyl-N-methoxy carboxamide (D16) (3.7 g, 0.020 mole) in dry tetrahydrofuran (50 ml) was cooled to −60° C. under an atmosphere of nitrogen and treated with 1.5M diisobutyl aluminium hydride in toluene (17.5 ml, 0.026 mole). The reaction was allowed to warm to −20° C. over a period of 1.45 h, cooled to −60° C. and added to a vigorously stirred solution of 5N hydrochloric acid (50 ml) at −20° C. The mixture was then concentrated in vacuo to remove the tetrahydrofuran and adjusted to pH 11 with solid aqueous potassium carbonate. The precipitated aluminium hydroxide was dissolved up by adding saturated sodium potassium tartrate and the aldehyde product recovered by extracting with chloroform (4×100 ml). The organic extracts were dried over sodium sulphate and concentrated in vacuo to a gum which was distilled (b.p. 90°–100° C. at 0.5 mmHg) to afford the title compound as a colourless oil (D10, 1.93 g, 77%).

$^1$H NMR (CDCl$_3$) δ: 1.05–1.35 (1H, m), 1.5–1.8 (1H, m), 2.2–2.95 (7H, m), 3.1 (1H, m), 9.75 (1H, s).

DESCRIPTION 11

(±) 2-[3-(1-Azabicyclo[2.2.1]hept-3-yl)-3-hydroxy-2-(4-methylphenylsulphonyl)propyl]1,3-dioxolane (D11)

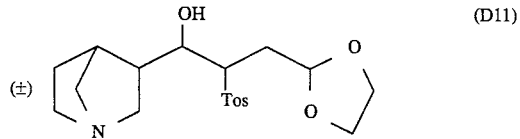

Crude (±) exo-1-azabicyclo[2.2.1]hept-3-ylcarboxaldehyde (D10, 1.0 g) was treated as in the method of Description 6 to give an orange oil (5.1 g), which contained the title compound (D11). This was used without purification.

DESCRIPTION 12

(±)2-[3(1-Azabicyclo[2.2.1]hept-3-yl)-3-hydroxy-2-(4-methylphenylsulphonyl)propyl]-2-methyl-1,3-dioxolane (D12)

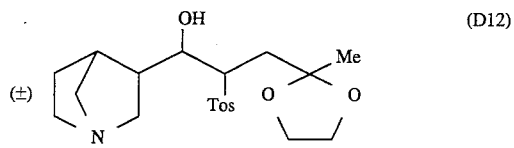

Crude (±) exo-1-azabicyclo[2.2.1]hept-3-ylcarboxaldehyde (D10, 0.92 g) was treated as in the method of Description 8 to give a pale yellow solid (5.6 g), which contained the title compound (D12). This was used without purification.

DESCRIPTION 13

(±)1-[3-(1-Azabicyclo[2.2.2]octane)]-butan-1,3-dione sodium salt (D13)

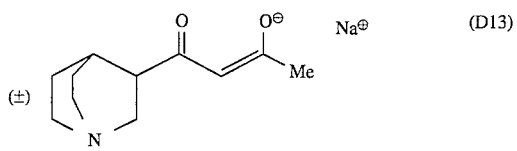

A solution of (±)3-acetyl-1-azabicyclo[2.2.2]octane (D2, 1.54 g, 0.01 mole) in toluene was dried azeotropically using a Dean and Stark trap. The dried solution (30 ml) was treated under nitrogen with sodium hydride (0.30 g of an 80% dispersion in oil, 0.01 mole), ethyl acetate (1.5 ml, 0.015 mole) and a drop of ethanol. After gentle warming for approx. 1 h the mixture was refluxed for 8 h. Additional portions of sodium hydride (0.1 g of 80% dispersion, 0.003 mole) and ethyl acetate (1.0 ml, 0.01 mole) were added after 2 h. The reaction was diluted with dry ether. Filtration afforded the title compound (D13) as a yellow solid (1.45 g, 67%) which was used in the next stage without purification.

DESCRIPTION 14

(±) 3-(α-Aminoacetyl)-1-azabicyclo[2.2.2]octane dihydrochloride (D14)

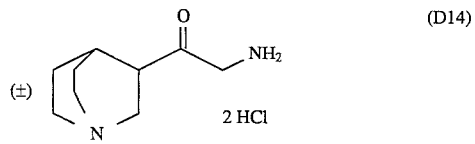

A solution of (±) 3-acetyl-1-azabicyclo[2.2.2] octane (D2) (10.6 g; 0.069 mol) in diethyl ether (250 ml) was treated with excess hydrogen bromide gas. The solvent was removed in vacuo and the residue dissolved in methanol (250 ml) and treated with bromine (10.9 g, 0.069 mol) at 0° C. and allowed to warm to room temperature over 48 h. Distilled water (200 ml) was then added to the reaction at 0° C. which was then concentrated to a gum whilst kept below 40° C. The gum was dissolved in dry dimethylformamide (250 ml) and treated with sodium azide (10.6 g, 0.16 mole) at 0° C. The reaction was allowed to warm to room temperature over 3 h and then rapidly concentrated under high vacuum to a gum. The gum was then partitioned between chloroform and saturated aqueous potassium carbonate solution and the organic layer separated, dried over sodium sulphate and rapidly concentrated under high vacuum with the temperature of the solution kept below 30° C. The resulting chloroform-free gum was immediately dissolved in methanol (300 ml) and treated with concentrated hydrochloric acid (30 ml), followed by 10% palladium on carbon (3.0 g), and the mixture hydrogenated at atmospheric pressure for 15 h. The catalyst was then filtered off and the filtrate concentrated in vacuo to a gum which was triturated with methanol/ether, whereupon the title compound dihydrochloride salt (D14) crystallised as needles (6 g; 40%) m.p. 250°–252° C. (dec).

¹H Nmr (d₆-DMSO) δ: 1.72 and 2.02 (each 2H, m, 5-C$\underline{H}_2$ and 8-C$\underline{H}_2$); 3.05–3.60 (8H, m, 2-C$\underline{H}_2$, 7-C$\underline{H}_2$, 6-C$\underline{H}_2$, 3-C$\underline{H}$, 4-C$\underline{H}$), 4.02 and 4.30 (2H, each d, J=15Hz, 10-C$\underline{H}_2$); 8.42 (3H, bs, NH₃), and 10.70 (1H, bs, NH).

¹³C Nmr (d₆-DMSO) δ: 18.6 and 22.8, 5-C and 8-C; 22.4, 4-C; 43.3, 3-C; 45.0, 45.2, 45.2 and 45.9 2-C, 6-C, 7-C, 10-C; 202.9, 9 $\underline{C}$=O

DESCRIPTION 15

(±) 3-[α-(Acetylamino)acetyl]-1-azabicyclo[2.2.2]octane (D15)

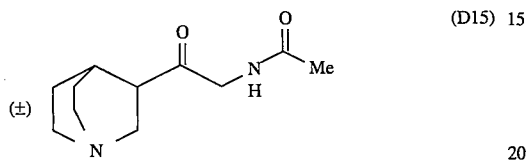

A suspension of the dihydrochloride salt of (±) 3-(α-aminoacetyl)-1-azabicyclo[2.2.2]octane (D14) (0.8 g; 0.0033 mole) in absolute chloroform (30 ml) was treated with acetyl chloride (0.76 g, 0.01 mole) and pyridine (4.58 g, 0.058 mole) at 0° C. for ½ h. The reaction was allowed to warm to room temperature for 15 h and then concentrated in vacuo. The residue was partitioned between chloroform and saturated aqueous potassium carbonate solution. The organic phase was separated, dried over sodium sulphate and concentrated in vacuo to a gum, which was chromatographed on neutral alumina in 10% methanol in ethyl acetate. This afforded the title compound as an oil (0.4 g, 58%).

¹H Nmr (CDCl₃) δ: 1.43 and 1.66 (each 2H, m, 5-C$\underline{H}_2$ and 8-C$\underline{H}_2$); 2.05 (3H, s, C$\underline{H}_3$); 2.15 (1H, m, 4-CH); 2.65–2.95 (6H, m, 2-C$\underline{H}$, 7-C$\underline{H}_2$ and 6-C$\underline{H}_2$); 3.35 (1H, qd, J=6Hz, J=2Hz, 2-C$\underline{H}$); 4.05 and 4.3 (each 1H, dd, J=18Hz, J=3Hz, —COC$\underline{H}_2$); 6.27 (1H, bs, N$\underline{H}$).

DESCRIPTION 16

(±) exo-1-Azabicyclo[2.2.1]hept-3-yl-N-methyl-N-methoxy carboxamide (D16)

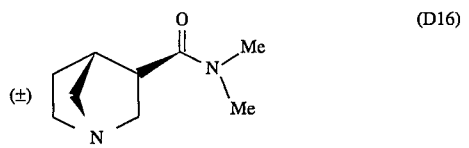

(±) exo-Ethyl-1-azabicyclo[2.2.1]hept-3-ylcarboxylate (D9) (8.0g, 0.047 moles) in hydrochloric acid (5N, 250 ml) was heated under reflux for 1.5 h. The reaction was then concentrated in vacuo to a solid which was dissolved in thionyl chloride (200 ml) and heated under reflux for 0.5 h when the copious evolution of sulphur dioxide and hydrogen chloride ceased. The reaction was then concentrated in vacuo to a gum, which was freed from excess thionyl chloride by co-evaporation with toluene. The residue was dissolved in dry acetonitrile (200 ml) under an atmosphere of nitrogen and treated with N,O-dimethylhydroxylamine hydrochloride (5 g, 0.05 mole). After cooling to 0° C. pyridine (18 g, 0.230 mole) was added dropwise. The reaction was allowed to warm to room temperature over a period of 16 h. The solvent was then removed in vacuo and the residue partitioned between saturated aqueous potassium carbonate solution and chloroform. The organic phase was separated, dried over sodium sulphate and concentrated in vacuo to a gum, which was distilled in vacuo to afford the title compound (3.1 g, 36%) Bp 150° C. at 0.1 mmHg.

¹H Nmr (CDCl₃) δ: 1.2 and 1.6 (each 1H, m, 5-C$\underline{H}_2$); 2.33 (1H, m, 4-H); 2.5 (2H, m); 2.7–3.0 (5H, m); 3.18 (3H, s, N-C$\underline{H}_3$); 3.70 (3H, s, O—C$\underline{H}_3$)

DESCRIPTION 17

(±) exo- and endo-3-Acetyl-1-azabicyclo[2.2.1]heptane (D17)

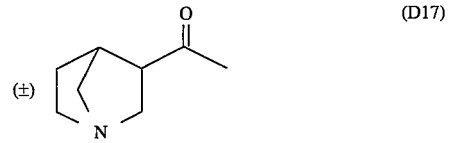

A solution of (±) exo-1-azabicyclo[2.2.1]hept-3-yl-N-methyl-N-methoxy carboxamide (D16) (3.10 g, 0.168 mole) in dry tetrahydrofuran (65 ml) was cooled to 0° C. and treated with methyl lithium in hexane (11.1 ml, 1.6M, 0.017 mole) under an atmosphere of nitrogen for 1.5 h. The reaction was then quenched by the addition of acetic acid (3 ml) and concentrated in vacuo. The resulting gum was then partitioned between saturated aqueous potassium carbonate solution and chloroform. The organic phase was separated, dried over sodium sulphate and concentrated in vacuo to a gum, which was distilled at 150° C. and 0.2 mmHg to afford the title compound (D17) (1.5 g, 65%) as a 9:1 mixture of exo and endo isomers.

¹H Nmr (CDCl₃) (signals corresponding to major exo isomer) δ: 1.2 and 1.6 (each 1H, m, 5-C$\underline{H}_2$); 2.1 (1H, m, 4-C$\underline{H}$); 2.18 (3H, s, C$\underline{H}_3$); 2.2–2.9 (6H, m, 3-C$\underline{H}$, 2-C$\underline{H}$, 6-C$\underline{H}_2$, 7-C$\underline{H}_2$); 3.0 (1H, d,d,d, J=12Hz, 6Hz, 3Hz, 2-C$\underline{H}$)

DESCRIPTION 18

(±) exo- and endo-3-(α-Aminoacetyl)-1-azabicyclo[2.2.1]heptane dihydrochloride (D18)

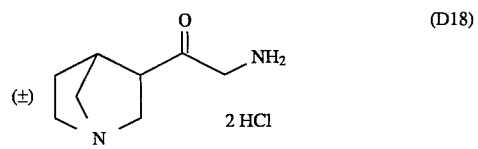

A solution of (±) exo- and endo-3-acetyl-1-azabicyclo[2.2.1]heptane (D17) (1.5 g, 0.01 mole) in ether (100 ml) was treated with excess hydrogen bromide gas. The solvent was then removed in vacuo and the residue dissolved in methanol (50 ml). To this solution was added bromine (1.71 g, 0.011 mole) and the reaction allowed to stand at room temperature for 24 h. A further quantity of bromine (0.85 g, 0.005 mole) was added and after standing at room temperature for a further 24 h, water (50 ml) was added and the reaction concentrated in vacuo to a gum at a temperature below 40° C. The residue was dissolved in dry dimethyl formamide (50 ml) and treated with sodium azide (1.65 g, 0.025 mole) at 0° C. The reaction was allowed to warm to room temperature over 3 h and then concentrated under high vacuum at a temperature below 40° C. The residue was partitioned between aqueous potassium carbonate solution and chloroform and the organic layer separated, dried over sodium sulphate and concentrated under high vacuum at a temperature below 30° C. The residue was immediately dissolved in methanol (100 ml) and treated with concentrated hydrochloric acid (5 ml) and 10% palladium on charcoal (0.3 g). The mixture was then hydrogenated at atmospheric pressure for 15 h, the catalyst filtered off and the solution concentrated in vacuo to a gum. Trituration with methanol/ether afforded the title compound dihydrochloride salt (D18) as needles (1.71 g, 68%). M.p. 225°–230° C.

$^1$H Nmr (d$_6$-DMSO) (Signals corresponding to major exo isomer) δ: 2.05 (1H, m); 2.32 (1H, m); 3.13 (1H, d, J=8Hz); 3.40 (1H, d, J=8Hz); 3.45–3.70 (6H, m); 4.25 and 4.55 each (1H, d, J=16Hz)

DESCRIPTION 19

(±) exo and endo-1-[3-(1-Azabicyclo[2.2.1]heptane)]butan-1,3-dione sodium salt (D19)

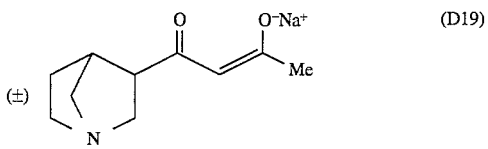

(±) exo and endo-3-Acetyl-1-azabicyclo[2.2.1]heptane (D17) (0.80 g; 5.75 mmole) was dissolved in sodium-dried toluene (25 ml) and treated with ethyl acetate (1.42 ml; 14.5 mmole), sodium hydride (80% dispersion in oil) (267 mg; 8.9 mmole) and a drop of ethanol. The solution was refluxed with stirring for 1.5 h, cooled and diluted with an equal volume of sodium-dried diethyl ether. The beige precipitate was filtered off and dried in vacuo to yield the title product (D19) as a pale yellow solid (0.99 g; 85%). This material was used in the next stage without purification.

DESCRIPTION 20

(±) 3-(Fur-3-yl)-3-hydroxy-1-azabicyclo[2.2.2]octane (D20)

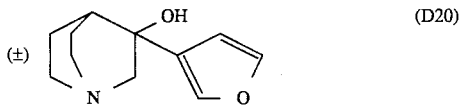

A stirred solution of 3-bromofuran (5.0 g of technical grade, 0.034 mole) in dry ether (130 ml) at −60° C. under nitrogen was treated with 1.6M n-butyllithium in hexane (18.7 ml, 0.030 mole) and then stirred for 5 minutes. A solution of 1-azabicyclo[2.2.2]octan-3-one (3.37 g, 0.027 mole) in dry ether (10 ml) was added and the resulting mixture stirred for 40 minutes at −60° C., then allowed to warm to room temperature. The mixture was treated with potassium carbonate solution (100 ml) and extracted with ethyl acetate (2×100 ml). The combined extracts were dried (Na$_2$SO$_4$) and concentrated in vacuo to leave a yellow oil, which was chromatographed on basic alumina eluting with ethyl acetate. The pale yellow oil obtained crystallised on standing. This material was recrystallised from acetone to give the title compound (D20) as a white solid (1.40 g, 21%) m.p. 130°–133° C.

$^1$H Nmr (CDCl$_3$) δ: 1.35–1.55 (3H, m), 1.95–2.05 (1H, m), 2.10–2.25 (1H, m), 2.55–3.25 (7H, m), 6.40–6.50 (1H, m), 7.35–7.50 (2H, m).

DESCRIPTION 21

(±) exo and endo-3-Oxo-3-[(1-azabicyclo[2.2.1]hept-3-yl]propanal sodium salt (D21)

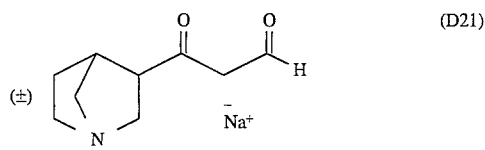

(±) exo and endo-3-Acetyl-1-azabicyclo[2.2.1]heptane (D17) (910 mg, 6.55 mmol) was dissolved in sodium-dried toluene (30 ml) and sodium hydride (80% dispersion in oil) (556 mg, 18.5 mmol) was added, followed by ethyl formate (1.54 ml, 19 mmol) and a drop of ethanol. The mixture was heated at reflux for 1 h, after which all starting material had been consumed. The mixture was diluted with twice the volume of sodium-dried ether, and the resulting suspension filtered to yield the title compound as a yellow/red solid (1.24 g, quantitative). This material was used in the next stage without purification.

DESCRIPTION 22

(±) 1-Azabicyclo[2.2.2]oct-3-yl-N-methyl-N-methoxy carboxamide (D22)

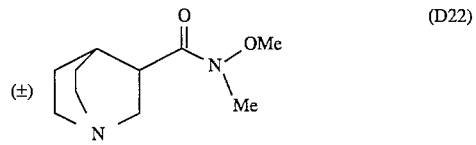

A solution of (±) 3-cyano-1-azabicyclo[2.2.2]-octane (D1) (6.3 g, 0.046 mole) in concentrated hydrochloric acid (80 ml) was heated under reflux for 4 h and then concentrated in vacuo to leave a yellow gum. This was dissolved in methanolic hydrogen chloride (100 ml) and heated under reflux for 2 h, then concentrated in vacuo to give an orange oil. This oil was treated with excess saturated potassium carbonate solution and extracted with chloroform (2×100ml). The combined extracts were dried over sodium sulphate and concentrated in vacuo to give an orange oil, which was distilled in a Kugelröhr apparatus (b.p. 120° C. at 0.2 mmHg) to give the methyl ester (6.83 g) as a colourless oil. A solution of this ester (2.0 g, 0.012 mole) in 8M hydrochloric acid (80 ml) was heated under reflux for 3 h, then concentrated in vacuo to leave a beige solid. This was treated with thionyl chloride (30 ml) and heated under reflux for 2 h, then concentrated in vacuo. The residue was dissolved in dry acetonitrile (100 ml) under nitrogen, treated with N,O-dimethylhydroxylamine hydrochloride (1.45 g, 0.015 mole), then cooled to −40° C. and treated dropwise over 5 minutes with dry pyridine (4.8 ml, 0.060 mole). The mixture was allowed to warm up to room temperature over 2 h, then concentrated in vacuo and the residue partitioned between potassium carbonate solution and chloroform. The organic layer was separated, dried over sodium sulphate and concentrated in vacuo to leave a brown oil, which was distilled in a Kugelröhr apparatus (b.p. 150° C. at 0.4 mmHg) to give the title compound as a colourless oil (1.45 g, 54%).

¹H NMR (CDCl₃) δ: 1.27–1.41 (1H, m), 1.55–1.67 (2H, m), 1.75–1.90 (1H, m), 2.00–2.07 (1H, m), 2.70–3.05 (6H, m), 3.20 (3H, s), 3.20–3.32 (1H, m), 3.69 (3H, s).

EXAMPLE 1

(±) 3-(1,2-Oxazol-5-yl)-1-azabicyclo[2.2.2]octane (E1)

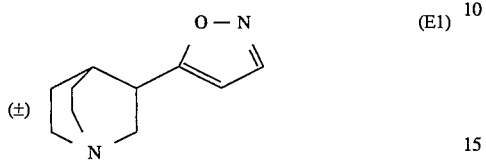

A suspension of (±) 3-oxo-3-(1-azabicyclo[2.2.2]oct-3-yl)propanal sodium salt (D3) (0.4 g; 2.0 mmoles) in dry ethanol (10 ml) was treated with potassium hydrogen sulphate (0.81 g; 6.0 mmoles) and sulphuric acid (0.2 g; 2.0 mmoles) to give a solution of pH 6. Hydroxylamine-O-sulphonic acid (0.25 g; 2.2 mmoles) in dry ethanol (25 ml) was added dropwise. After stirring at room temperature for 3 h the reaction was concentrated in vacuo. The residue was treated with saturated potassium carbonate solution (15 ml) and extracted into ether (4×20 ml). The combined extracts were washed (brine), dried (Na₂SO₄) and concentrated to give 0.26 g of crude product. Chromatography on neutral alumina using chloroform as eluant afforded the title compound (E1) as a colourless oil (0.15 g; 44%) which was converted into the oxalate salt, m.p. 109°–110° C. (acetone).

Oxalate: Ir (KBr) νC=N 1560 cm⁻¹

¹H NMR (d₆-DMSO) 1.50–1.80 (2H, m), 1.80–2.10 (2H, m), 2.30 (1H, m), 3.10–3.50 (5H, m), 3.55–3.78 (2H, m), 6.63 (1H, s), 8.56 (1H, s).

¹³C NMR (d₆-DMSO) 18.50, 22.75, 24.52, 31.82, 45.13, 45.34, 48.57, 101.33, 150.96, 164.59, 171.38.

Analysis: C₁₂H₁₆N₂O₅ requires C: 53.73; H: 6.01; N: 10.44 found C: 53.81; H: 5.93; N: 10.48

EXAMPLE 2

(±) 3-(Fur-2-yl)-1-azabicyclo[2.2.2]octane (E2)

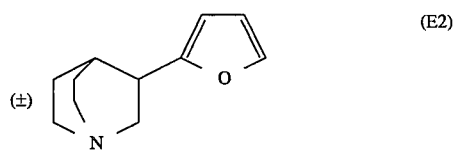

A stirred solution of crude (±) 2-[3-(1-azabicyclo[2.2.2oct-3-yl)-3-hydroxy-2-(4-methylphenylsulphonyl)propyl]1,3-dioxolane (D6, 7.7 g) in glacial acetic acid (150 ml) was heated under reflux for 48 h. The solution was concentrated in vacuo and the residue basified with saturated potassium carbonate solution and extracted with chloroform (2×100 ml). The combined extracts were dried (Na₂SO₄) and concentrated in vacuo to leave a dark brown oil, which was chromatographed on a basic alumina column eluting with ethyl acetate. The material obtained was purified further by chromatography on a silica gel column eluting with 5–15% methanol/chloroform, followed by distillation in a Kugelröhr apparatus to give the title compound (E2) as a colourless oil (440 mg) b.p. 170°–180° C. at 0.35 mm. This was converted into its oxalate salt.

Oxalate: ¹H NMR (d₆-DMSO) δ: 1.70–1.85 (2H, m), 1.95–2.15 (2H, m), 2.25–2.35 (1H, m), 3.20–3.60 (6H, m), 3.65–3.80 (1H, m), 6.50–6.60 (2H, m), 7.70–7.75 (1H, m).

EXAMPLE 3

(±) 3-(5-Methyl-fur-2-yl)-1-azabicyclo[2.2.2]octane (E3)

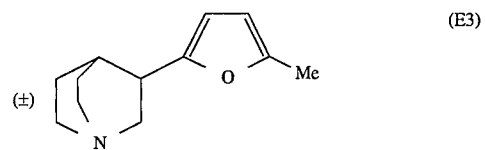

A stirred solution of crude (±) 2-[3-(1-azabicyclo[2.2.2]oct-3-yl)-3-hydroxy-2-(4-methylphenylsulphonyl) propyl]-2-methyl-1,3-dioxolane (D8, 11.1 g) in glacial acetic acid (250 ml) was heated under reflux for 18 h. The solution was concentrated in vacuo and the residue basified with potassium carbonate solution and extracted with chloroform (2×100 ml). The combined extracts were dried (Na₂SO₄) and concentrated in vacuo to leave a brown oil, which was chromatographed on silica gel eluting with 0–20% methanol/chloroform. The yellow oil obtained was distilled in a Kugelröhr apparatus to give the title compound (E3) as a colourless oil (660 mg) b.p. 180°–190° C. at 0.25 mm. This was converted into its hydrochloride salt m.p. 171°–173° C.

Hydrochloride: ¹H Nmr (d₆-DMSO) δ: 1.60–1.75 (2H,m), 1.80–2.00 (2H,m), 2.10–2.20 (1H,m), 2.23 (3H,s), 3.05–3.45 (6H,m), 3.50–3.65 (1H,m), 6.00–6.07 (1H,m), 6.32–6.38 (1H,m).

Analysis: C₁₂H₁₇NO.HCl. Requires C:63.30; H:7.90; N:6.15. Found C:63.20; H:8.00; N:6.15.

EXAMPLE 4

(±) exo-3-(Fur-2-yl)-1-azabicyclo[2.2.1]heptane (E4)

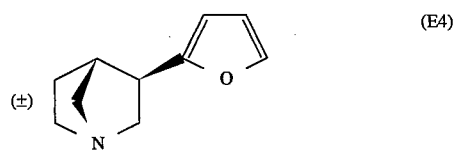

A stirred solution of crude (±) 2-[3-(1-azabicyclo[2.2.1]hept-3-yl)-3-hydroxy-2-(4-methylphenylsulphonyl)propyl]-1,3-dioxolane (D11, 5.1 g) in glacial acetic acid (200 ml) was heated under reflux for 30 h. The solution was concentrated in vacuo and the residue basified with potassium carbonate solution and extracted with chloroform (2×80 ml). The combined extracts were dried (Na₂SO₄) and concentrated in vacuo to leave a dark brown oil, which was chromatographed twice on basic alumina eluting with ether. The yellow oil obtained was distilled in a Kugelröhr apparatus to give the title compound (E4) as a colourless oil (210 mg) b.p. 140°–145° C. at 0.2 mm. This was converted to its hydrochloride salt m.p. 160°–163° C.

Hydrochloride: ¹H Nmr (d₆-DMSO) δ: 1.70–1.85 (1H,m), 1.95–2.10 (1H,m), 2.85–2.95 (1H,m), 3.05–3.45 (6H,m), 3.55–3.70 (1H,m), 6.35–6.45 (2H,m), 7.58–7.65 (1H,m), 11.40 (1H,brs).

Analysis: C₁₀H₁₃NO.HCl Requires C:60.15; H:7.00; N:7.00. Found C:60.20; H:6.90; N:7.00.

EXAMPLE 5

(±) exo-3-(5-Methyl-fur-2-yl)-1-azabicyclo[2.2.1]heptane (E5)

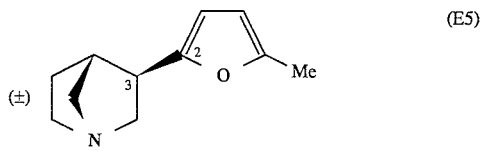

A stirred solution of crude (±)2-[3-(1-azabicyclo[2.2.1]hept-3-yl)-3-hydroxy-2-(4-methylphenylsulphonyl)propyl]-2-methyl-1,3-dioxolane (D12, 5.6 g) in glacial acetic acid (200 ml) was heated under reflux for 1.5 h. The solution was concentrated in vacuo and the residue basified with potassium carbonate solution and extracted with chloroform (2×80 ml). The combined extracts were dried ($Na_2SO_4$) and concentrated in vacuo to leave an orange oil, which was chromatographed on silica gel eluting with 0–7% methanol/chloroform. The pale yellow oil obtained was distilled in a Kugelröhr apparatus to give the title compound (E5) as a colourless oil (350 mg) b.p. 140°–150° C. at 0.1 mm. This was converted into its hydrochloride salt m.p. 139°–141° C.

Hydrochloride: $^1$H Nmr ($d_6$-DMSO) δ: 1.70–1.83 (1H,m), 1.90–2.10 (1H,m), 2.23 (3H,s), 2.85–2.95 (1H,m), 3.05–3.40 (6H,m), 3.55–3.65 (1H,m), 6.00–6.07 (1H,m), 6.20–6.27 (1H,m), 11.25 (1H,brs).

Analysis: $C_{11}H_{15}NO.HCl$ requires C:61.80; H:7.55; N:6.55. found C:61.40; H:7.60; N:6.60.

EXAMPLE 6

(±)3-(3-Methyl-1,2-oxazol-5-yl)-1-azabicyclo[2.2.2]octane (E6)

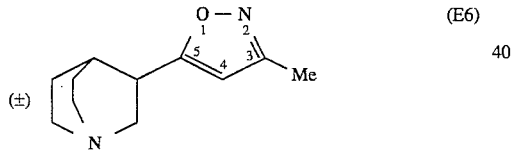

A solution of (±)1-[3-(1-azabicyclo[2.2.2]octane)]-butan-1,3-dione sodium salt (D13, 1.35 g, 6.2 mmole) in dry ethanol (50 ml) was cooled in ice and treated with p-toluenesulphonic acid (12.4 ml of an anhydrous 1M solution in toluene obtained by azeotropic drying). After rapid addition of a solution of hydroxylamine-O-sulphonic acid (0.70 g, 6.2 mmole) in dry ethanol (50 ml) the reaction was stirred at room temperature for 1 h and then heated at 40° C. for 3 h followed by a further 2 h at 60° C. The reaction was concentrated in vacuo and the residue was treated with saturated potassium carbonate solution. Extraction into chloroform (3×25 ml) followed by drying and concentration in vacuo afforded a brown oil (0.9 g) which was extracted into ether and then distilled on a Kugelröhr at approx. 175° C./0.2 mmHg to give the title compound (E6) as a colourless oil (0.65 g, 55%).

Ir (KBr) νC=N 1600 cm$^{-1}$.

$^1$H Nmr (CDCl$_3$) δ: 1.40 (1H,m), 1.50–1.78 (3H,m), 2.10 (1H,m), 2.30 (3H,s), 2.75–3.10 (6H,m), 3.30 (1H,m), 5.90 (1H,s).

$^{13}$C Nmr (CDCl$_3$) δ: 11.51, 21.65, 25.64, 26.97, 34.97, 46.99, 47.50, 52.21, 101.21, 159.63, 175.40.

Hydrochloride: m.p. 210°–211° C. (from acetone-methanol).

Analysis: $C_{11}H_{16}N_2O.HCl$ Requires C:57.76; H;7.49; N:12.25. Found C:57.44; H:7.56; N:12.14.

EXAMPLE 7

(±) 3-(2-Methyl-1,3-oxazol-5-yl)-1-azabicyclo[2.2.2]octane (E7)

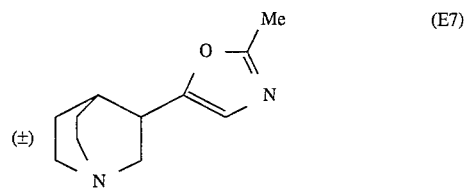

(±) 3-[α-(Acetylamino)acetyl]-1-azabicyclo [2.2.2]octane (D15) (0.4 g, 0.002 mole) in polyphosphoric acid (20 g) was heated from 110°–160° C. over a period of 15 min. The reaction mixture was poured onto ice, basified with aqueous potassium carbonate and the product recovered by extraction into chloroform. Kugelröhr distillation afforded the title compound (E7) (100 mg, 27%) b.p. 180°–190° C. at 0.1 mmHg and m.p. 50°–52° C.

$^1$H Nmr (CDCl$_3$) δ: 1.34 (1H, m) and 1.62 (3H, m), together 5-C$\underline{H}_2$ and 8-C$\underline{H}_2$; 1.95 (1H, m, 4-C$\underline{H}$); 2.35 (3H, s, C$\underline{H}_3$); 2.82 (6H, m, 2-C$\underline{H}_2$, 6-C$\underline{H}_2$, 7-C$\underline{H}_2$); 3.20 (1H, m, 3-C$\underline{H}$); 6.62 (1H, s, 4'-C$\underline{H}$)

The hydrochloride salt crystallised from acetone-ether as flakes, m.p. 185°–187° C.

$^1$H Nmr (CDCl$_3$) δ: 1.84 (1H, m) and 2.10 (3H, m) together 5-C$\underline{H}_2$ and 8-C$\underline{H}_2$; 2.40 (1H, m, 4-C$\underline{H}$); 2.45 (3H, s, C$\underline{H}_3$), 3.40 (6H, m, 2-C$\underline{H}_2$, 6-C$\underline{H}_2$ and 7-C$\underline{H}_2$); 3.7 (1H, m, 3-C$\underline{H}$); 6.83 (1H, s, 4'-C$\underline{H}$) and 12.53 (1H, m, N$\underline{H}$).

EXAMPLE 8

(±) exo- and endo-3-(2-Methyl-1,3-oxazol-5-yl)-1-azabicyclo[2.2.1]heptane (E8a) and (E8b)

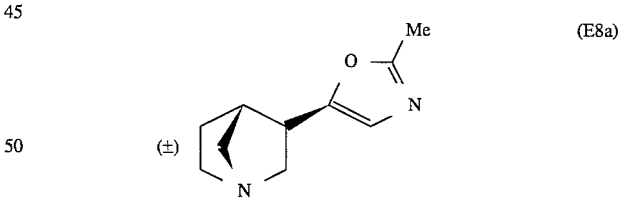

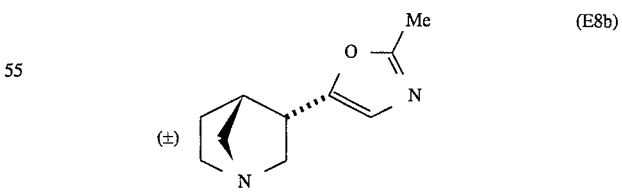

(±) exo and endo-3-(α-Aminoacetyl)-1-azabicyclo[2.2.1]heptane dihydrochloride salt (D18) (0.5 g, 0.0022 mole) was suspended in dry acetonitrile (30 ml) under an atmosphere of nitrogen, and treated with acetyl chloride (0.38 g, 0.0048 mole) and pyridine (1.28 g, 0.016 mole) at 0° C. with continuous stirring. The reaction was stirred for 1 h at 25° C. and then concentrated in vacuo to a gum, which was partitioned between saturated aqueous potassium carbonate solution and chloroform. The organic layer was separated, dried over sodium sulphate and concentrated in vacuo. The residue was mixed with polyphosphoric acid (20 g) and heated from 110° to 160° C. over 15 minutes and held at this temperature for 15 minutes. The reaction was then allowed to cool to room temprature and poured into aqueous potassium carbonate solution. The product was recovered by extraction into chloroform. The residue on evaporation was chromatographed on silica in a gradient of 0–5% methanol in chloroform. Pooling of pure fractions containing the faster running component afforded the exo isomer (E8A) as a pale yellow oil (65 mg; 18%) which was converted into the oxalate salt m.p. 143°–144° C. (from acetone-methanol).

Oxalate salt:

$^1$H Nmr (d$_6$-DMSO) δ: 1.75 (1H, m), 2.02 (1H, m), 2.37 (3H, s), 2.90 (1H, m), 3.03–3.21 (3H, m), 3.31 (3H, m), 3.53 (1H, m), 6.98 (1H, s).

$^{13}$C Nmr (d$_6$-DMSO) δ: 13.52, 26.79, 36.83, 40.54, 51.29, 56.02, 56.74, 122.72, 151.34, 160.59, 164.51

Analysis: $C_{12}H_{16}N_2O_5$ requires C: 53.71; H: 6.01; N: 10.44%. found C: 53.84; H: 6.14; N: 10.42%.

Fractions containing the slower running component afforded the endo isomer as an oil (20 mg; 6%) which was converted into the oxalate salt.

Oxalate salt:

$^1$H Nmr (d$_6$-DMSO) δ: 1.40 (1H, m), 1.85 (1H, m), 2.37 (3H, s), 2.98–3.80 (SH, m), 7.06 (1H, s).

$^{13}$C Nmr (d$_6$-DMSO) δ: 13.61, 22.01, 35.45, 39.69, 51.82, 53.91, 58.91, 124.23, 149.30, 161.20, 163.50.

EXAMPLE 9

(±) exo-3-(3-Methyl-1,2-oxazol-5-yl)-1-azabicyclo[2.2.1]heptane

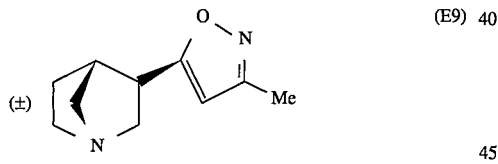

A solution of (±) exo and endo-1-[3-(1-azabicyclo[2.2.1]heptane)]-butan-1,3-dione sodium salt (D19) (0.98 g; 4.82 mmole) in dry ethanol (45 ml) was adjusted to pH6 by addition of an anhydrous solution of p-toluenesulphonic acid, which was obtained by azeotropic drying. Hydroxylamine-o-sulphonic acid (0.55 g; 4.83 mmole) in dry ethanol (30 ml) was added, and a white precipitate formed. After 1 h the reaction mixture was concentrated in vacuo and the residue dissolved in aqueous saturated potassium carbonate solution (60 ml) and extracted with ethyl acetate (2×250 ml). The organic extracts were dried (Na$_2$SO$_4$) and evaporated to dryness in vacuo to yield a yellow semisolid (0.62 g). This was purified by column chromatography using basic alumina and eluting with diethyl ether. Pooling of fractions containing the major faster running product afforded the title compound (D9) (91 mg; 10%), which was converted into the oxalate salt.

Oxalate salt:

$^1$H Nmr (d$_6$-DMSO) δ: 1.78 and 2.03 (each 1H, m), 2.20 (3H, s, C$\underline{H}_3$), 2.50 (1H, m), 2.99–3.30 (6H, m), 3.61 (1H, m), 6.41 (1H, s).

$^{13}$C Nmr (d$_6$-DMSO) δ: 11.0, 26.9, 37.6, 40.8, 51.2, 56.5, 57.0, 102.4, 159.6, 164.0, 171.8.

Mass spectrum $C_{10}H_{14}N_2O$; requires 178.1106 found 178.1107

EXAMPLE 10

(±) 3-(Fur-3-yl)-1-azabicyclo[2.2.2]octane (E10)

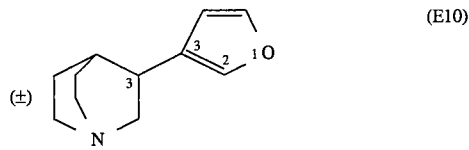

A stirred solution of (±) 3-(fur-3-yl)-3-hydroxy-1-azabicyclo[2.2.2]octane (D20) (1.20 g, 0.0062 mole) in an acetonitrile (20 ml)/dichloromethane (10 ml) mixture was treated with triethylsilane (5.9 ml, 0.037 mole) and cooled to −30° C. under nitrogen. The solution was treated dropwise over 5 minutes with tin (IV) chloride (1.6 ml, 0.0136 mole) and then allowed to warm to room temperature over 0.5 h, before pouring into excess potassium carbonate solution and extracting with ethyl acetate (2×60 ml). The combined extracts were dried (Na$_2$SO$_4$), concentrated in vacuo and the residue eluted through a short basic alumina column with ether. The yellow oil obtained was then chromatographed on silica gel eluting with 0 to 20% methanol/chloroform to give the title compound (E10) as a pale yellow oil (150 mg, 10%). This was converted into its hydrochloride salt and recrystallised from methanol/ether m.p. 179°–182° C.

Hydrochloride: $^1$H NMR (d$_6$-DMSO) δ: 1.60–1.80 (2H, m), 1.80–2.15 (3H, m), 3.05–3.40 (6H, m), 3.50–3.65 (1H, m), 6.53–6.60 (1H, m), 7.62–7.70 (1H, m), 7.76 (1H, s), 10.70 (1H, br, s).

Analysis: $C_{11}H_{15}NO.HCl$ requires C: 61.85; H: 7.50; N: 6.55. Found: C: 62.00, H: 7.50; N: 6.45.

EXAMPLE 11

(±) 3-(1,3-Oxazol-5-yl)-1-azabicyclo[2.2.2]octane (E11)

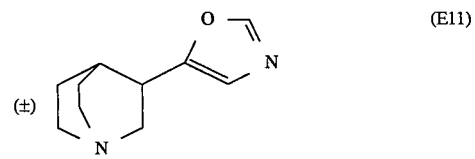

A solution of (±) 1-azabicyclo[2.2.2]oct-3-yl-carboxyaldehyde (D4) (1.01 g, 0.01 mole) in methanol (15 ml) was treated with p-toluenesulphonylmethylisocyanide (1.33 g, 0.01 mol) and potassium carbonate (1.00 g, 0.01 mole) under nitrogen. The reaction mixture was heated under reflux with vigorous stirring for 60 minutes, then concentrated in vacuo and partitioned between chloroform and saturated aqueous potassium carbonate solution. The organic phase was separated, dried (Na$_2$SO$_4$) and then concentrated in vacuo to an oil (A). A solution of the crude oil (A) in ether (5 ml) was added to polyphosphoric acid (20 g) and then ether removed in vacuo. The resulting sludge was heated to 160° C. on an oil bath, stirring vigorously. After being held at 160° C. for 10 mins the reaction mixture was cautiously poured into a vigorously stirred emulsion of chloroform (100 ml) and saturated aqueous potassium carbonate solution (100 ml). The resulting mixture was treated with solid potassium carbonate until strongly alkaline. The organic phase was separated, dried (Na₂SO₄), combined and concentrated in vacuo to a brown oil. Distillation (b.p. 117° C. at 0.1 mmHg) afforded the title product (E11) as a colourless oil which crystallised on cooling (0.75 g, 58%).

Treatment of the base in ether with hydrogen chloride gas in ether afforded the hydrochloride as a hygroscopic solid.

$^1$H NMR (Free Base) (CDCl₃) δ: 1.32–1.8 (4H, m, 5-CH₂ and 8-CH₂), 2.05 (1H, m, 4-H), 2.75–3.13 (6H, m, 2-CH₂, 7-CH₂, 6-CH₂), 3.3 (1H, t, J=12Hz, 3-CH), 6.86 (1H, s, 4'-CH), 7.85 (1H, s, 2'-CH).

$^{13}$C NMR (CDCl₃) δ: 21.5 and 26.9, C-5 and C-8; 25.5, C-4; 33.7, C-3; 46.9, 47.4 and 51.7, C-2, C-6 and C-7; 150.3, C-4'; 121.6, C-2'; 155.1, C5'.

EXAMPLE 12

(±) exo and endo-3-(1,3-Oxazol-5-yl)-1-azabicyclo[2.2.1]heptane (E12)

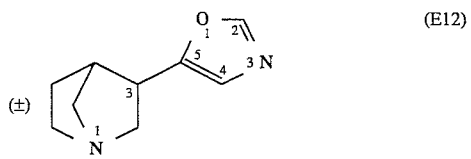

(±) Exo and endo-1-Azabicyclo[2.2.1]hept-3-yl carboxaldehyde (D10) (1 g, 0.008 mole) in dry methanol (20 ml) was treated with p-toluenesulphonylmethylisocyanide (1.56 g, 0.008 mole) and anhydrous potassium carbonate (1.1 g, 0.08 mole) under an atmosphere of nitrogen and heated under reflux for 0.5 h with continuous stirring. The reaction was concentrated in vacuo to a gum which was partitioned between saturated aqueous potassium carbonate and chloroform. The organic layer was separated, dried over sodium sulphate and concentrated in vacuo to a gum (1.3 g). The gum was then mixed with polyphosphoric acid (20 g) and plunged into an oil bath at 165° C. for 10 minutes with continuous stirring. The reaction was then allowed to cool and poured into a well stirred mixture of chloroform and excess saturated aqueous potassium carbonate. The organic layer was separated, dried over sodium sulphate and concentrated in vacuo to a gum which was distilled on a Kugelrőhr (b.p. 150° C. at 0.1 mmHg) to afford a mixture of the title compounds (E12). $^1$H NMR showed an 88:12 mixture of exo:endo isomers which could not be separated by chromatography.

$^1$H NMR (CDCl₃) δ: 1.3 and 1.7 (each 1H, m, 5-CH₂), 2.33–3.0 (8H, m), 6.78 (1H, s, exo isomer 4'-CH), 6.82 (1H, s, endo isomer, 4'-CH), 7.8 (1H, s, exo 2'-CH), 7.85 (1H, s, endo, 2'-CH).

$^{13}$C NMR exo isomer (CDCl₃) δ: 30.0, C-5; 39.5, C-4; 42.1, C-3; 58.6, 58.15, 60.15, together C-2, C-6, C-7; 121, 4'-H; 150.2, 2'-H; 154.9, 5'-H.

$^{13}$C NMR endo isomer (CDCl₃) δ: 24.3, C-5; 38.2, 4-H; 41.6, 3-H; 54.4, 57.7, 61.0, (C-2, C-6, C-7); 122.6, C-4'; 150.4, C-2; 153.4, C-5'.

The hydrochloride salt of the mixture was prepared in the normal way to afford a very hygroscopic solid.

EXAMPLE 13

(±) exo-3-(1,2-Oxazol-5-yl)-1-azabicyclo[2.2.1]heptane (E13)

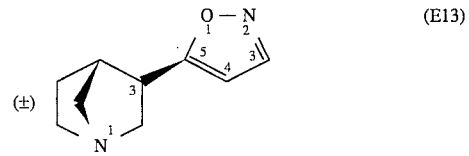

(±) exo and endo-3-Oxo-3-[(1-azabicyclo[2.2.1]hept-3-yl)]propanal sodium salt (D21) (1.24 g, 6.56 mmol) was dissolved in EtOH (70 ml) and the pH adjusted to 6 using 1M tosic acid in toluene (azeotropically dried). Hydroxylamine-O-sulphonic acid (0.78 g, 6.89 mmol) was dissolved in EtOH and added to the yellow suspension. The suspension turned white in colour and further white precipitate formed. The mixture was stirred for 75 min at room temperature and the suspension was evaporated to dryness under reduced pressure. The residue was dissolved in aqueous saturated potassium carbonate (30 ml) and extracted with ethyl acetate (2×300 ml). The organic extracts were combined, dried (sodium sulphate), filtered and evaporated to dryness under reduced pressure to yield a yellow solid (790 mg). Trituration with diethyl ether yielded a yellow oil (260 mg, 24%) and this was further purified by column chromatography using basic alumina and eluting with diethyl ether. A proportion of the eluted product was combined to give the title compound (54 mg), which was crystallised as the oxalate salt.

$^1$H NMR (270 MHz, d₄-MeOH) 2.00 (1H, m), 2.26 (1H, m), 3.18 (1H, d), 3.20–3.80 (7H, bm), 6.40 (1H, d, isoxazole CH) and 8.32 (1H, d, isoxazole CH)

MS C₉H₁₂N₂O, M⁺ found 164.0950, required 164.0953.

EXAMPLE 14

(±) 3-(2-Ethyl-1,3-oxazol-5-yl)-1-azabicyclo[2.2.1]heptane (E14)

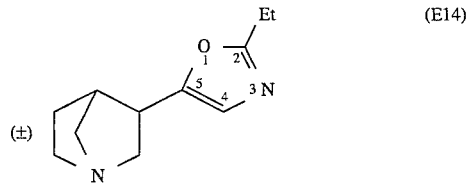

(±) exo and endo-3-(α-Aminoacetyl)-1-azabicyclo[2.2.1]heptane dihydrochloride (D18) (0.51 g, 2.2 mmol) was suspended in dry acetonitrile (30 ml) and cooled to 0° C. Propionyl chloride (0.35 ml, 4.0 mmol) was added slowly, followed by pyridine (KOH dried) (0.89 ml, 11 mmol) added dropwise over 5 mins. The suspension was stirred at room temperature for 45 mins, evaporated to dryness under reduced pressure, dissolved in saturated aqueous potassium carbonate and extracted with ethyl acetate (2×200 ml). The organic extracts were combined, dried (sodium sulphate), filtered and evaporated to dryness under reduced pressure to yield a yellow syrup. This was mixed with polyphosphoric acid (20 ml) and placed in an oil bath at 110° C. The temperature was increased to 160° C., and the mixture stirred at this temperature for 30 mins. The syrup was then poured carefully onto solid potassium carbonate mixed with ice and the basic aqueous layer extracted with ethyl acetate (2×500 ml). The organic layers were dried (sodium sulphate), filtered and evaporated to dryness under reduced pressure to yield a brown oil (320 g). This was purified by column chromatography using basic alumina and eluting with diethyl ether to give a mixture of exo and endo isomers of the title compound (180 mg, 43%) which was purified further by column chromatography using fine TLC grade neutral alumina and eluting with chloroform. A proportion of the fractions was combined to give the higher running exo isomer as a syrup (50 mg) which was purified as the oxalate salt.

$^1$H NMR (270 MHz, d$_6$DMSO) 1.32 (3H, t, C$\underline{H}_3$CH$_2$—), 1.85 (1H, m), 2.10 (1H, m), 2.82 (2H, q, CH$_3$C$\underline{H}_2$—), 3.01 (1H, d), 3.13–3.50 (6H, bm), 3.67 (1H, bm), 5.0–6.0 (bs, oxalate CO$_2\underline{H}$) and 7.08 (1H, s, oxazole-C$\underline{H}$).

$^{13}$C NMR (67 MHz, d$_6$DMSO) 10.9 (CH$_3$), 20.9 (CH$_2$), 26.7 (CH$_2$), 36.8 (CH), 40.5 (CH), 51.4 (CH$_2$), 56.0 (CH$_2$), 56.8 (CH$_2$), 122.6 (CH), 151.1 (quart C), 164.2 (quart C), 164.8 (quart C).

MS C$_{11}$H$_{16}$N$_2$O, M$^+$ found 192.1263, required 192.1265

BIOLOGICAL ACTIVITY

Radio Ligand Binding

Cerebral cortex from Hooded Lister rats (Olac, UK) is homogenised in 2.5 vols ice-cold 50 mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H-OXO-M) experiments. For 3H-Quinuclidinyl Benzilate (3H-QNB), 1 ml of stored membranes is diluted to 30 ml and 0.1 ml mixed with test compound and 0.27 nM (c. 25,000 cpm) 3H-QNB (Amersham International). For 3H-OXO-M, 1 ml of membranes is diluted to 6 ml and 0.1 ml mixed with test compound and 2 nM (c. 250,000 cpm) 3H-OXO-M (New England Nuclear).

Non-specific binding of 3H-QNB is defined using 1 µM Atropine sulphate (2 µM Atropine) and of 3H-OXO-M using 10 µM Oxotremorine. Non-specific binding values typically are 5% and 25% of total binding, respectively. Incubations are carried out at 37° C. for 30 min and the samples filtered using Whatman GF/B filters. (In the 3H-OXO-M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as IC$_{50}$ values (i.e. the concentration which inhibits binding of the ligand by 50%) for the displacement of the muscarinic agonist 3H-OXO-M and the muscarinic antagonist 3H-QNB. The ratio IC$_{50}$(3H-QNB)/IC$_{50}$(3H-OXO-M) gives an indication of the agonist character of the compound. Agonists typically exhibit a large ratio; antagonists typically exhibit a ratio near to unity.

The results are shown in Table 1:

TABLE 1

| Compound | [$^3$H]-oxo-M IC$_{50}$ (nm) | [$^3$H]-QNB IC$_{50}$ (nm) |
|---|---|---|
| E1$^+$ | 477 | 15500 |
| E2$^+$ | 360 | 10000 |
| E4$^{++}$ | 88 | 7000 |
| E5$^{++}$ | 115 | 3200 |
| E6$^{++}$ | 395 | 4300 |
| E7$^{++}$ | 105 | 4400 |
| E8A$^+$ | 24 | 7500 |
| E9$^+$ | 102 | 7500 |
| E10$^{++}$ | 834 | 19500 |
| E11$^{++}$ | 480 | 24000 |
| E12$^{++}$ | 150 | 29000 |
| E13$^+$ | 173 | 30300 |
| E14 | 800 | 9600 |

$^+$Tested as the oxalate salt
$^{++}$Tested as the hydrochloride salt

We claim:

1. A compound of formula (I) or a pharmaceutically acceptable salt thereof:

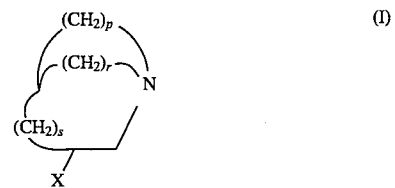

in which (p,r,s) is selected from among (2,2,0), (2,1,1), (3,1,1), (2,1,0), and (3,1,0); and X represents a group

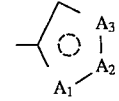

in which A$_1$ is oxygen or sulphur, one of A$_2$ and A$_3$ is CR$_1$ and the other is nitrogen or CR$_2$, or A$_2$ is oxygen or sulphur, A$_1$ is CH and A$_3$ is CR$_1$, where R$_1$ and R$_2$ are independently selected from hydrogen and C$_{1-2}$ alkyl, with the proviso that when r is 2, R$_1$ and R$_2$ are independently hydrogen or methyl.

2. A compound according to claim 1 wherein X is 1,2-oxazol-5-yl, 3-methyl-1,2-oxazol-5-yl, 1,3-oxazol-5-yl, 2-methyl-1,3-oxazol-5-yl, 2-ethyl-1, 3-oxazol-5-yl, furan-2-yl, furan-3-yl or 5-methyl-furan-2-yl.

3. A compound according to claim 1 wherein (p,r,s) is (2,2,1) or (2,1,1).

4. A compound of formula (1) according to claim 1 having two assymetric centres, in the exo configuration.

5. A compound selected from:

(±) 3-(1,2-Oxazol-5-yl)-1-azabicyclo[2.2.2]octane, (±) 3-(Fur-2-yl)-1-azabicyclo[2.2.2]octane, (±) 3-(5-Methyl-fur-2-yl)-1-azabicyclo[2.2.2]octane, (±) exo-3-(Fur-2-yl)-1-azabicyclo[2.2.1]heptane, (±) exo-3-(5-Methyl-fur-2-yl)-1-azabicyclo[2.2.1]heptane, (±) 3-(3-Methyl-1,2-oxazol-5-yl)-1-azabicyclo[2.2.2]octane, (±) 3-(2-Methyl-1,3-oxazol-5-yl)-1-azabicyclo[2.2.2]octane, (±) exo-3-(2-Methyl-1,3-oxazol-5-yl)-1-azabicyclo[2.2.1]heptane, (±) endo-3-(2-Methyl-1,3-oxazol-5-yl)-1-azabicyclo[2.2.1]heptane, (±) exo-3-(3-Methyl-1,2-oxazol-5-yl)-1-azabicyclo[2.2.1]heptane, (±) 3-(Fur-3-yl)-1-azabicyclo[2.2.2]octane, (±) 3-(1,3-Oxazol-5-yl)-1-azabicyclo[2.2.2]octane, (±) exo-3-(1,3-Oxazol-5-yl)-1-azabicyclo[2.2.1]heptane, (±) endo-3-(1,3-Oxazol-5-yl)-1-azabicyclo[2.2.1]heptane, (±) exo-3-(1,2-Oxazol-5-yl)-1-azabicyclo[2.2.1]heptane, and (±) 3-(2-Ethyl-1,3-oxazol-5-yl)-1-azabicyclo[2.2.1]heptane, or a pharmaceutically acceptable salt thereof.

6. A pharmaceutical composition for the treatment or prophylaxis of dementia in humans comprising a therapeutically effective amount of a compound according to claim 1 and a pharmaceutically acceptable carrier.

7. A method of treatment or prophylaxis of dementia in mammals, which comprises administering to the patient an effective amount of a compound of formula (I) as defined in claim 1.

* * * * *